United States Patent [19]

Hansen et al.

[11] Patent Number: 5,968,088
[45] Date of Patent: *Oct. 19, 1999

[54] EXPANDABLE STENT

[75] Inventors: Palle M. Hansen, Roskilde, Denmark; Timothy G. Vendrely, Lafayette, Ind.; Dale Berry, West Lafayette, Ind.; Coy M. Herald, Lafayette, Ind.

[73] Assignee: William Cook, Europe A/S, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/813,650

[22] Filed: Mar. 7, 1997

Related U.S. Application Data

[60] Provisional application No. 60/012,999, Mar. 7, 1996.

[51] Int. Cl.$^6$ ..................................................... A61F 2/06
[52] U.S. Cl. ................................................. 623/1; 606/194
[58] Field of Search ..................... 606/191, 195, 606/198, 194; 523/1, 12

[56] References Cited

U.S. PATENT DOCUMENTS

| | | | |
|---|---|---|---|
| 4,856,516 | 8/1989 | Hillstead | 128/343 |
| 5,102,417 | 4/1992 | Palmaz | 623/11 |
| 5,344,426 | 9/1994 | Lau et al. | 606/198 |
| 5,354,308 | 10/1994 | Simon et al. | 606/198 |
| 5,370,683 | 12/1994 | Fontaine | 623/1 |
| 5,395,390 | 3/1995 | Simon et al. | 623/1 |
| 5,397,355 | 3/1995 | Marin et al. | 623/12 |
| 5,449,373 | 9/1995 | Pinchasik et al. | |
| 5,496,365 | 3/1996 | Srgo | 623/1 |
| 5,562,697 | 10/1996 | Christiansen | 623/1 |
| 5,591,197 | 1/1997 | Orth et al. | 623/1 |
| 5,593,442 | 1/1997 | Klein | 623/1 |
| 5,630,829 | 5/1997 | Lauterjung | 606/198 |

FOREIGN PATENT DOCUMENTS

| | | |
|---|---|---|
| 0221570 | 1/1991 | European Pat. Off. . |
| 0423916 | 4/1991 | European Pat. Off. . |
| 0480667 | 4/1992 | European Pat. Off. . |
| 0556850 | 8/1993 | European Pat. Off. . |
| 0566807 | 10/1993 | European Pat. Off. . |
| 0622088 | 11/1994 | European Pat. Off. . |
| 0645125 | 3/1995 | European Pat. Off. . |
| 0669114 | 8/1995 | European Pat. Off. . |
| 3918736 | 12/1990 | Germany . |
| 3342798 | 10/1992 | Germany . |
| 4303181 | 8/1994 | Germany . |
| 9216166 | 10/1992 | WIPO . |
| 9313825 | 7/1993 | WIPO . |
| 9403127 | 2/1994 | WIPO . |
| 9412136 | 6/1994 | WIPO . |
| 9417754 | 8/1994 | WIPO ........................................ 623/1 |
| 9503010 | 2/1995 | WIPO ........................................ 623/1 |
| 9531945 | 11/1995 | WIPO . |
| 9614028 | 5/1996 | WIPO . |

OTHER PUBLICATIONS

Cook–Z® Stents, "Gianturco–Rösch Covered Esophageal Design," William Cook Europe, (Date Unknown).
Cook–Z™ Stents, "Gianturco–Rösch Biliary Design," Cook Incorporated 1989.

*Primary Examiner*—Michael Buiz
*Assistant Examiner*—David O. Reip
*Attorney, Agent, or Firm*—Richard J. Godlewski

[57] ABSTRACT

An expandable endovascular stent comprises a flexible, tubular body (1) with a longitudinal axis, the wall of which is formed by interconnected, closed lattice cells (2) arranged with at least two cells adjacent to each other in the circumferential direction. Filament-shaped lattice material capable of transmitting compressive forces in the axial direction of the filament extends continuously from one lattice cell directly into the lattice cell following in the longitudinal direction. The stent can be expanded from a radially compressed state into a radially expanded state having a larger diameter. In the expanded state of the stent, the pressure transmitting lattice material in several of the lattice cells (2) forms a heart-like or arrowhead-like shape with at least two interconnected diverging, angle β cell sides (5) positioned opposite to and interconnected with at least two mutually converging, angle α longer cell sides (3). For stability during expansion and compression of a self-expanding stent, the sum of the first angle α and the second angle β should be in the range of 345° to 360°, preferably at 360° to maintain a constant axial stent length.

25 Claims, 9 Drawing Sheets

EXPANDABLE STENT

RELATED APPLICATIONS

This application claims priority of provisional application Ser. No. 60/012,999, filed Mar. 7, 1996.

TECHNICAL FIELD

This invention relates generally to medical devices and, in particular, to an expandable stent.

BACKGROUND

One expandable stent is known from German patent No. 33 42 798, where the lattice cells are formed by sets of wires extending helically through the body at opposite winding directions. The lattice cells are rhomboidal, and the stent length changes substantially at the expansion, which gives rise to several disadvantages, one being that it is difficult to position the stent accurately, another that the insertion system is complicated.

U.S. Pat. No. 5,370,683 describes a stent formed from a single filament which is wrapped around a mandril in a wavy course having alternating short and long, elongated pieces of filament, whereupon the filament is arranged in a helical course with the wave troughs mutually aligned. Then the wave troughs have been interconnected to form rhomboidal lattice cells having a pair of opposite short cell sides and another pair of opposite long cell sides. Among other things, this stent is distinguished in being capable of compression into a radially compressed state without the stent ends having to be pulled apart. The stent can be arranged in a catheter in a radially compressed state and be inserted and positioned at the desired site in a lumen, such as a blood vessel, whereupon the catheter can be pulled away and the stent be expanded by means of an inflatable balloon arranged inside the stent. It is a disadvantage of the stent that it has relatively poor bending flexibility, as this reduces the adaptability of the stent to the supported, flexible vessel. Nor is it an advantage that the cells of the stent are relatively open and thus more exposed to fibrous in-growth into the inner lumen of the stent.

In a stent known from EP-A 645125, a tubular stent body is also formed from a single angularly bent filament wound in a spiral shape with the apexes hooked into each other to form rhomboidal cells. Because the apexes are only hooked into each other, there is a risk of compression of the stent in the longitudinal direction if it is pushed out of the catheter. The two ends of the filament are returned through the stent body in a spiral course, but do not remove the risk of longitudinal changes in the part of the stent which is expanding outside the end of the catheter. It may, therefore, be necessary to pull the stent out of the catheter by means of a pulling device passing centrally through the stent body and restricting its compression inside the catheter. The flexibility of the stent at bending is also relatively poor, and the cells are very open.

A number of different stents of another type is also known, in which the cell material does not continue directly from one lattice cell to the following one in the longitudinal direction. Instead, this type of stent is constructed from several Z-shape-bent wires joined into a tubular body by means of connecting threads or being hooked into each other, vide EP-A 622088, EP-A 480667, WO93/13825 and EP-A 556850. All these stents are of limited bending flexibility and some of them are very complicated to manufacture. The connecting threads for joining the Z-bent, resilient lattice material limit the expanded stent diameter, but yield completely to axial pressure. This results in the substantial disadvantage that impacts on a cell are not transferred to the cell following in the longitudinal direction, so that the stent has discontinuous properties, can open up and will exhibit breaks at bending.

Stents constructed from wires wound about each other to form closed cells are known from DE-A 39 18 736, where the cells are elongated or Ω-shaped, and from WO94/03127, where the cells are oval in the circumferential direction.

SUMMARY OF THE INVENTION

The foregoing problems are solved and a technical advance is achieved in an illustrative expandable stent in which there is minimal, if any, lengthening or shortening of the stent between radially compressed or expanded states. The stent comprises a flexible, tubular-shaped body with a longitudinal axis, the wall of the body being formed by interconnected, closed lattice cells arranged with at least two cells laterally adjacent to each other, each lattice cell having first mutually converging cell sides. The body includes filament-shaped lattice material in which the stent is expandable from a radially compressed state into a radially expanded state having a larger diameter.

Advantageously, the stent can be compressed and expanded radially without any substantial change of the length of the body, and which has a lattice structure providing the stent with a higher, uniform bending flexibility and thus higher vascular adaptability. Furthermore, the stent also has a compressive strength which is suitably high and adapted to the application in question.

In view of this, the stent according to the present invention is characterized in that the lattice material in several of the lattice cells forms a heart-like or arrowhead-like shape with second interconnected cell sides positioned opposite and connected with the first mutually converging cell sides.

In the heart-like or arrowhead-like shape, the point of interconnection between the second cell sides points towards the point of interconnection between the first cell sides of the same cell. Among other things, this provides the considerable advantage that when the center axis of the stent is laterally bent, the cells are deformed on the outer side of the curvature so that the angle facing into the cell between the second cell sides becomes smaller, and the cells become more open with a larger cell length.

This can occur at a very small bending moment, because the cells can expand without simultaneous contraction of the surrounding cells. The smaller angle between the second cell sides at the same time increases the stresses thereof directed in the circumferential direction and counteracts the reduction of the radial compressive strength of the stent on the outer side of the curvature generated by the lower cell density here. The high bending flexibility of the stent and its ability to maintain considerable radial compressive strength even at a sharp curvature of its longitudinal axis provide the stent with a large vascular compatibility, permit positioning of the stent in areas with vascular curvatures or other vascular variations and presumably counteract long-term damage to the vascular wall caused by the inserted stent.

The many closed cells give the stent evenly distributed uniform properties, and the cell shape or cell shapes are relatively dense, which counteracts re-stenosis or other lumen reduction of the vessel.

At radial compression of the stent, the first converging cell sides fold together about the second cell sides. At full compression about a guide wire, the stent has a configuration where the cell sides are packed tightly about the longitudinal axis of the stent and extend substantially in parallel with it. This provides an advantageous possibility of positioning the stent in a catheter with a small internal diameter. A stent with a diameter of 8 mm can, for example, be compressed for positioning in a catheter with an internal lumen of 7 French (about 2.3 mm).

With a suitable choice of the stent material, the stent is self-expanding when the catheter is removed following insertion of the compressed stent. The self-expanding capability is mainly obtained owing to the bending stresses occurring at the bending of the cell sides near their ends. The result of the lattice cell shape is that bending normally occurs at six points in the cell contrary to the four points in a rhomboidal cell, and thus the stent can have a more uniform and finer distribution of the expansion forces. Alternatively, or in supplement, the stent can be expanded by means of an inflatable balloon. The self-expanding stent need not be compressed radially about a balloon, and therefore during insertion it may be positioned in a thinner catheter.

At the folding together of the lattice cells, the cell sides of a cell are laid down into the neighboring cells without having to displace them in the longitudinal direction of the stent. This means that at the change between the compressed and the expanded state, the stent has substantially unchanged length apart from a negligible change in length at the end of the stent where the cell sides are not laid down into following cells. The stable length is advantageous when positioning the stent, as it can be positioned accurately in the vasoconstriction before release. When the catheter is retracted and the stent is released, the lattice cells can expand to their final position in contact with the vascular wall approximately without any longitudinal displacement of the ends of the stent. Therefore, the introducer system can be of a simple design and extremely easy to operate. The only requirement is a pusher which can be held in stationary contact with the end of the compressed stent nearest the insertion opening, while the catheter is retracted. The simple introducer system reduces the risk of erroneous positioning of the stent and is rapid in use.

It is possible to orient the points of the hearts in an oblique angle so that they point along a helical line in the periphery of the body. In consideration of compact compression of the stent, the arrowheads or heart points preferably face in the longitudinal direction of the body, and the interval between two neighboring lattice cells with the same orientation of the arrowheads or heart points consists of a lattice cell with an opposite orientation of the arrowhead or point. The interconnection between the neighboring cells in this design extends in the longitudinal direction of the stent.

In a preferred embodiment, the lattice cells adjacent to each other in an annular row in the circumferential direction of the body have alternatingly oriented arrowheads or heart points and constitute a lattice pattern repeated along the length of the body. In this design, the interconnections between adjacent cells in one circumferential row extend in axial extension of the arrowheads or points in the next circumferential row, and all lattice cells have the advantageous shape which gives the stent uniform properties, such as uniform torsional, bending and compression rigidities.

The cells can extend in a helical pattern along the length of the body by both the second cell sides and also the first converging cell sides having equal or mutually different lengths. However, in consideration of the manufacture of the stent, the second cell sides preferably have substantially the same length, and the first converging cell sides have substantially the same length.

The first angle $\alpha$ between the first converging cell sides and facing into the cell, together with the number of cells in the circumferential direction of the body, determines the bending rigidity of the body. With the same number of cells in an annular row, a smaller first angle $\alpha$ provides a greater distance between the cells in the longitudinal direction and thus greater bending rigidity and a more open lattice structure. The first angle $\alpha$ can be in the range of 20° to 160°. If the first angle $\alpha$ is smaller than 20°, the stent can only expand to a slightly larger diameter than the compressed state. If the first angle $\alpha$ is larger than 160°, very large changes in diameter can be obtained, but the number of cells in the longitudinal direction becomes unsuitably large. The first angle $\alpha$ is preferably in the range of 60° to 120°, providing an advantageously high flexibility combined with a suitable number of cells in the longitudinal direction. More preferably, the first angle $\alpha$ is 90°.

Provided that the arrowheads or points do not face in the circumferential direction, the second angle $\beta$ between the second cell sides and facing into the cell influences the compression rigidity of the body, the density of the lattice structure and the extra increase of diameter to which the body can be exposed after the normal expansion to a larger diameter. Such an extra diameter increase into an overexpanded state can, for example, be very advantageous if a self-expanding stent has been inserted into a vessel where re-stenosis occurs. Following the re-stenosis diagnosis, an inflatable balloon can be inserted into the stent and inflated to a large diameter without having to remove the stent, the stent merely being overexpanded by the balloon, only to return to its normal shape when the balloon is removed. The possibility of over-expansion can also be used at the insertion of the stent, as the stent can be positioned inside a hard stenosis before balloon dilation thereof. At the subsequent balloon dilation, the stent helps to keep the hardest stenosis area out at the desired diameter when the balloon is removed. This avoids dilation before the stent is positioned. At over-expansion, it is a substantial advantage that the stent does not change its length at the expansion. If the points of the heart-like or arrowhead-like lattice cells face in the circumferential direction, the second angle $\beta$ can suitably be at about 180°. If the points face in the longitudinal direction, the second angle $\beta$ should be larger than 184° so that the second cell sides are folded into the cell at compression of the stent. If the second angle $\beta$ is larger than 340°, and the filament is not of a large diameter, compression rigidity is largely absent. Preferably, the second angle $\beta$ is in the range of 210° to 320°, which provides a suitable compression rigidity, good density of cells and a possibility of overexpansion into a substantially larger diameter. The angles are chosen taking into account the field of application concerned. The closer the second angle is to 180°, the higher is the compression rigidity of the stent, but if the angle becomes substantially smaller than 210°, the possibilities of over-expansion become less favorable.

In a specially preferred embodiment, the first converging cell sides and the second cell sides all form an angle of between 10° and 45° with the longitudinal direction of the body. This renders it possible to compress the stent in a simple manner, either manually or by pushing the stent through a funnel-shaped loading sheet. It is particularly advantageous if the first converging cell sides form an angle of between 40° and 45° with the longitudinal direction.

When the sum of the first and the second angles $\alpha$ and $\beta$ is in a preferred range of 345° to 360°, the closed lattice cells of the stent advantageously remain stable during expansion and compression of the stent. As the sum lessens, the closed lattice cells of the stent become more and more unstable, producing unpredictable behavior such as the stent wall folding in or out and preventing deployment of the stent. More preferably, the sum of the angles α and β should be 360°. As a result, the axial length of the stent advantageously remains constant during expansion and compression. In such instance, the length of the first and the second cell sides are all the same. Otherwise, the first converging cell sides about first angle α are equal in length to each other, but longer in length than second cell sides. However, second cell sides limiting second angle β are equal in length to each other.

It is possible to render the stent more bending flexible in certain areas by the first angle α in the lattice cells being smaller in one area of the body than in another area of the body. This can be used, for example, to make the stent more flexible in the end areas so that the transition from the stent-affected to the non-affected area of the vascular wall becomes even, whereby the vascular wall is irritated as little as possible at the stent ends, and vascular injuries and tissue in-growth are counteracted. This is particularly advantageous if the risk of stent migration in the vessel is small.

It is also possible to design the stent so that the second angle β in the lattice cells is larger in one area of the body than in another area of the body, whereby the compressive strength of the stent can be varied according to desire. In case of hard stenoses, the second angle β can, for example, be larger at the end areas of the body so that the stent exerts the largest radial pressure at its middle, and the ends are softer and more adaptable to the vessel. It can also be desirable that the stent is fixed in the vessel by exerting a large contact pressure at the end areas and, in this case, the second angle β is then smaller than at the stent middle.

In some applications, it is desirable for the stent to have a bell or hourglass shape, which can be obtained in that at at least one end of the body the diverging and converging cell sides of the lattice cells are of greater length and/or the lattice cells have a smaller angle between the diverging cell sides than at the middle of the body, whereby the body has a larger diameter at the end than at the middle.

With a view to compressing the stent to a configuration with an advantageously small external diameter, it may be advantageous that the number of wires in the stent is not too high. If the stent is to be inserted by means of a catheter with a small diameter, the number of lattice cells in an annular row in the circumferential direction of the body preferably substantially corresponds to the radius of the body measured in mm. Substantially in this context means that for each four mm radius, the cell number can be one more or less than the radius measure in mm, viz. one cell more or less for a stent having a diameter of 6 mm, two more or less for a stent having a diameter of 10 mm, etc.

In a preferred embodiment, the body is formed by several filaments constituting the first and the second converging cell sides and being wound about each other at the adjacent ends of the pairs of first diverging or second converging cell sides, preferably so that each filament has a stepped spiral-like or a stepped wave-like course in the longitudinal direction of the body. The winding together of the filaments at the adjacent ends mutually locks the lattice cells, but at the same time provides the filaments with an advantageous possibility of bending apart from each other through opening of the windings when the stent is compressed radially, which reduces filament stresses at the points of interconnection. The result of the geometrical locking of the mutual position of the cells provided by the winding about is that in its compressed state the stent has a large axial rigidity so that it can be removed from the catheter without problems and without changes in length, when the catheter is retracted. In its expanded state, the winding about ensures that the stent has a stable shape in which the lattice cells do not slide in relation to each other at the application of external loads. The stent manufactured from filaments is relatively simple to manufacture, and the course of the filaments throughout the body can be selected so that the stent is both torsionally stable and pressure stable, for example, by the filaments having a spiral-like or wave-shaped course.

Alternatively, the body can be formed from a thin-walled tube or a thin-walled piece of plate in which the cell openings are fashioned, preferably by etching. The lattice cells are in this case fashioned in an integral piece of material, which can be done by machining alone. Alternatives to chemical etching or laser etching can be spark machining, laser cutting or punching of the thin-walled material, which are well-known methods for forming holes in such a material.

BRIEF DESCRIPTION OF THE DRAWING

Examples of embodiments of the stent according to the invention will now be described in further detail below with reference to the very schematic drawing, in which.

DETAILED DESCRIPTION

In the following description of non-limiting examples of embodiments of the invention, the same reference numerals will be used for elements having the same effect in the different embodiments.

Figure 5:
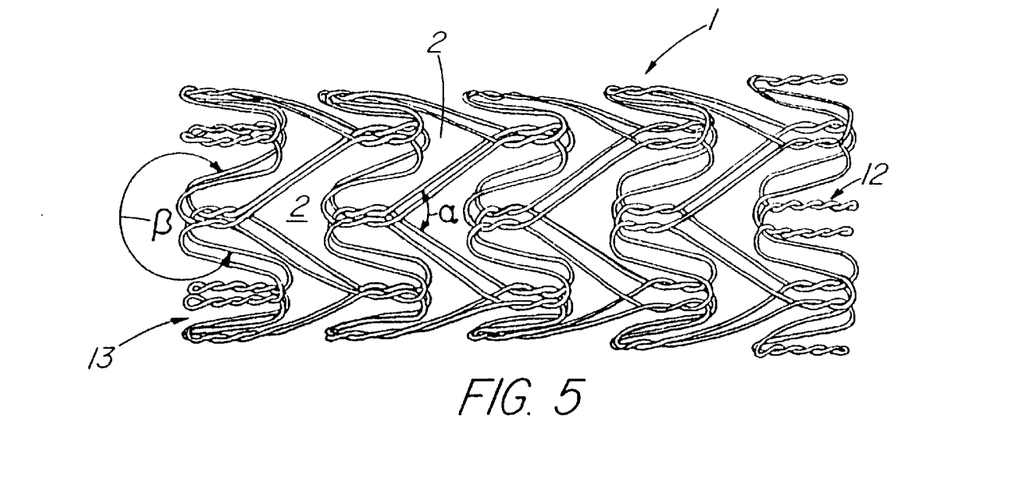
FIG. 5 is a side view of an embodiment of a whole stent according to the invention.

FIG. 5 shows a self-expanding stent in the form of a tubular-shaped body 1 formed of several filaments or wires bent to form heart-shaped lattice cells 2 and wound about each other at the places where the cell filaments meet so that the lattice cells are fixed to each other both in the longitudinal and the circumferential directions.

Figure 1:
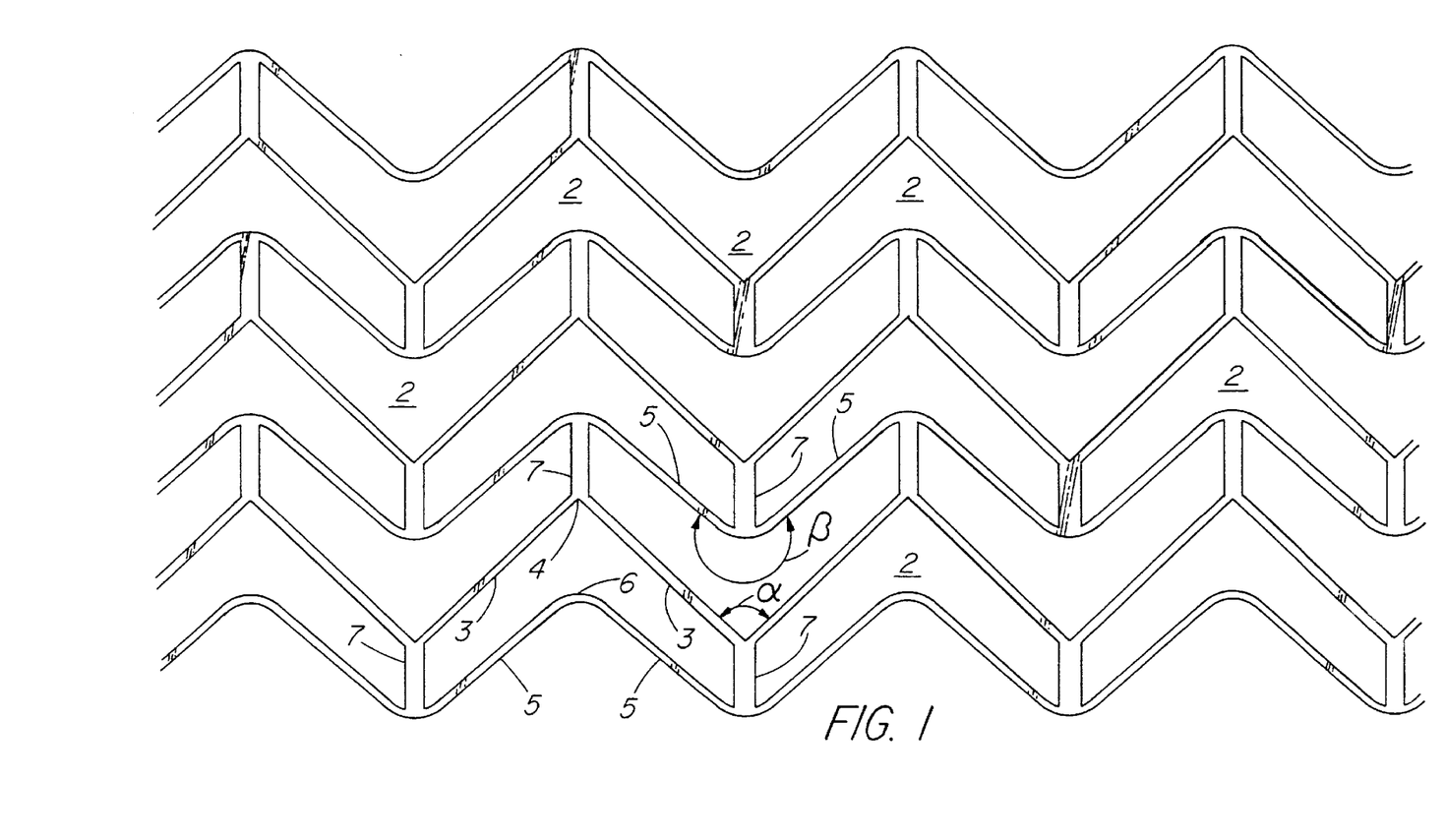
FIG. 1 shows a plane view of an unfolded section of the wall in a stent according to the invention made from thin-walled plate material.

FIG. 1 shows an example of heart-shaped lattice cells 2 fashioned in a thin-walled plate which can be formed into a tubular-shaped stent either before or after the fashioning. The fashioning can be done, for example, by etching or spark machining in a manner known in the art. Each lattice cell 2 has at least two mutually converging, first cell sides 3 converging into a unified filament at a point 4 of the heart and delimiting a first angle α facing into the cell. The lattice cell also has at least two second cell sides 5 converging with each other at a point area 6 positioned opposite the heart point 4. The second cell sides delimit a second angle β facing into the cell and they are positioned opposite to the first cell sides 3, with which they are connected through two side sections 7 to form the closed lattice cell of pressure-rigid lattice material. The first converging cell sides 3 can be and preferably are of equal length. Similarly, the second cell sides 5 can be and preferably are of equal length. First and second converging cell sides 3 and 5 can be and preferably are of equal length; however, first converging cell sides 3 are longer in length than second cell sides 5, particularly when the sum of first and second angles α and β are other than 360°. The length of the side sections 7 can be made larger or smaller, according to whether the cell is desired to be more or less open, without changing the sizes of the first or the second angle α, β. The shape of the side sections 7 can also be varied; they can, for example, be thinner, have an hourglass shape, I-shape, O-shape or any other shape, but the straight shape shown with a larger thickness than the first and second cell sides 3 and 5 is preferred owing to its simplicity and relatively high rigidity, resulting in the occurrence of any cell deformations mainly in the first and second cell sides 3 and 5. The heart point 4 can be more rounded and the point area 6 can be more pointed or more rounded than shown. It is also possible to insert a connecting section between the at least two mutually converging, first cell sides 3 so that the cell shape, for example, becomes more angular without any point areas proper. In the context of the invention, a heart-like or arrowhead-like shape means a closed cell having at one end a tapering shape facing out of the cell, and at the opposite end a more or less tapering shape facing into the cell.

The lattice pattern is constructed in such a manner that in the circumferential direction of the body there is an annular row of closed lattice cells 2 interconnected by the common side sections 7, and all having their points 4 oriented similarly in the longitudinal direction of the body. The first, typically longer cell sides 3 also constitute corresponding sides in an annular adjacent row in the longitudinal direction of the body and consisting of uniformly formed closed lattice cells having an opposite orientation of the points 4. These two cell rows constitute a common annular row of cells in which the points 4 have alternatingly opposite orientations and continue into the common side sections in the subsequent row. The stent length can be adapted to the desired application by varying the number of annular rows of cells.

In the preferred embodiment shown, the first angle α is about 90°, and the second angle β is about 263°, more preferably 270°. This gives the stent advantageously uniform properties, both as to bending and to compressive strength, because the first longer cell sides 3 and the second shorter cell sides 5 all form an angle of about 45° with the longitudinal direction of the body. At radial compression of the stent, the cell sides are therefore uniformly deformed, and the stresses are distributed evenly between the sides of the cell, which on expansion results in a uniform strong unfolding of all cells with a very low risk of erroneous unfolding and with a uniform resulting pressure influence on the vascular wall. Because the second angle β is typically smaller than the angle (360°-α) corresponding to a parallel course of the shorter and longer cell sides, the free distance between the point area 6 and the point 4 becomes suitably large so that on compression it can more easily receive the side section 7 from the subsequent lattice cell of the same orientation, when it is swung backwards and towards the longitudinal axis of the body. This promotes compact compression of the stent.

Figure 2:
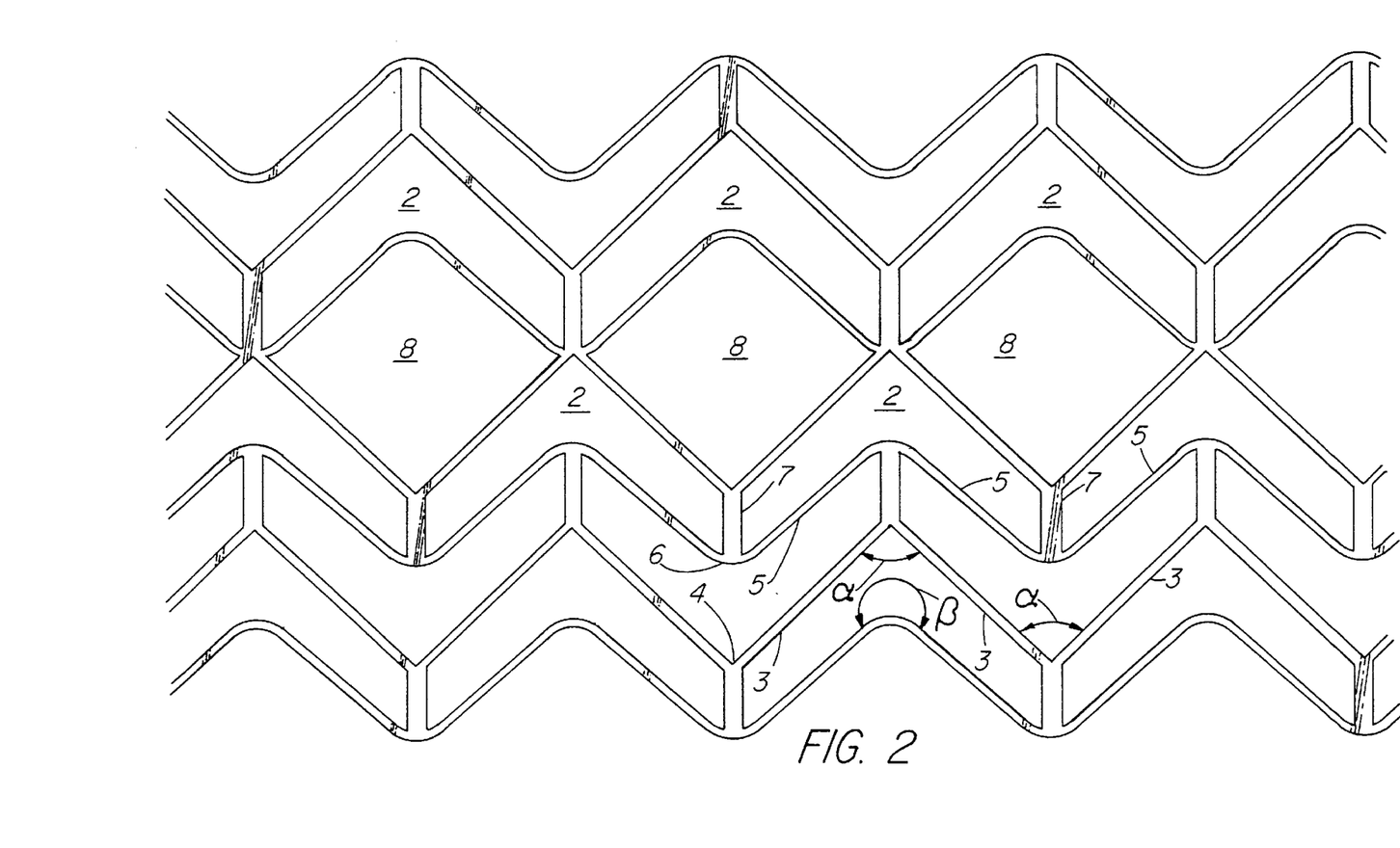
FIG. 2 shows a corresponding view of a second embodiment of the stent.

The embodiment shown in FIG. 2 deviates in that some of the cells do not have the advantageous heart-like or arrowhead-like shape, as a number of rhomboidal cells 8 are inserted in the cell pattern. This gives the stent an area with more open cells and substantially greater bending rigidity, which can, for example, be used for stabilizing undesired large local vascular movements. Naturally, it is also possible to give individual local cells another shape. This may be done in a simple manner by removing one or more cell sides in a cell.

Figure 3:
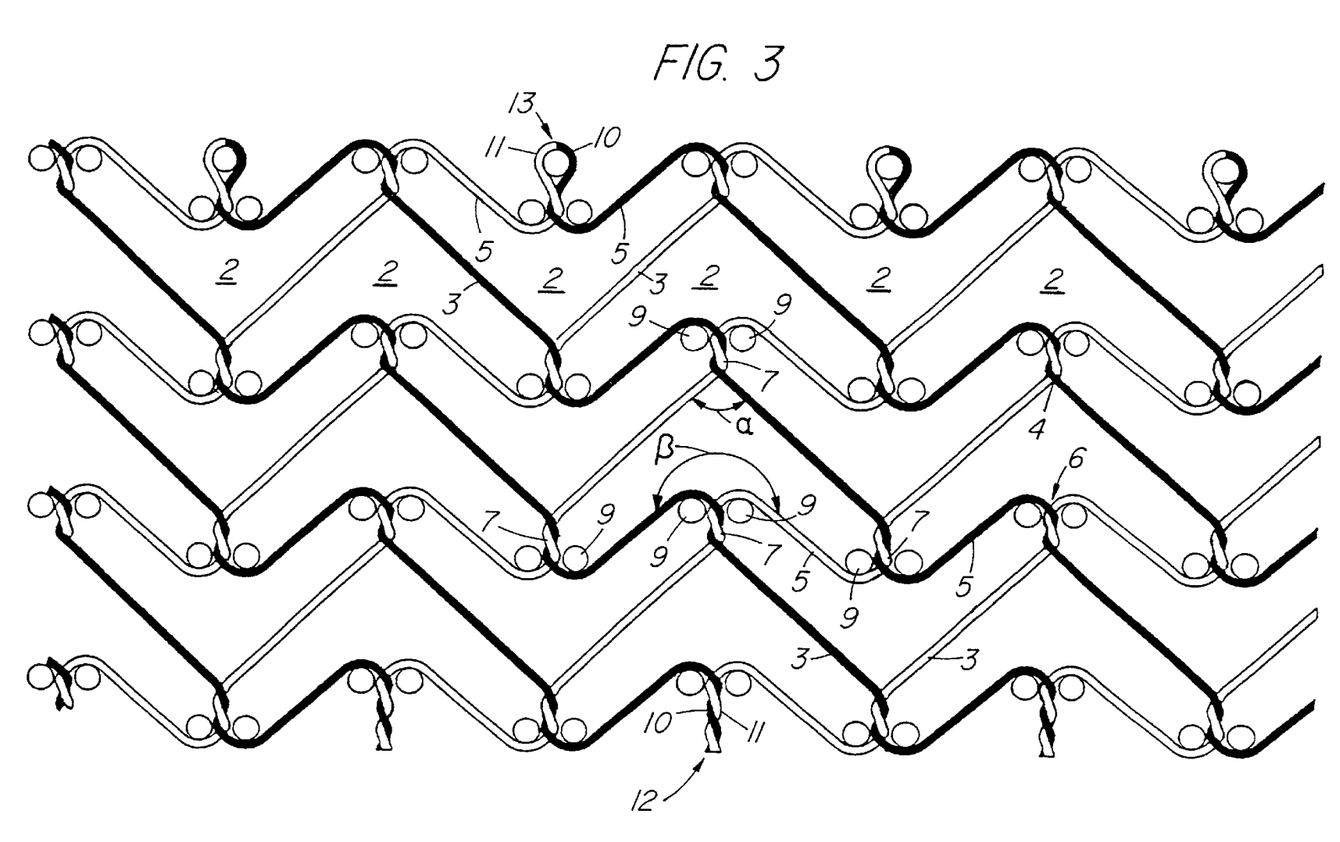
FIG. 3 is a view corresponding to that of FIG. 1 of the most preferred embodiment, in which the lattice cells have the same shape as in FIG. 1, and the stent is manufactured from several wound filaments.

In the embodiment of FIG. 3, the lattice cells 2, the first angle α and the second angle β have the same dimensions as in FIG. 1, but the body 1 is formed by filaments bent on a mandril around guide pins 9 and wound once around each other at the side sections 7. Owing to the structure with filaments, the cells have more rounded shapes, and the heart-like shape can assume a heart shape. For each lattice cell 2 in a circumferential row, two filaments 10, 11 extend from one end of the stent, which filaments can be wound about each other as a filament end 12 or can continue into each other in an eyelet 13. From the lattice cell at the end of the stent, each pair of two filaments 10, 11 extends along the body in a stepped spiral-like course with opposite directions of winding, in which the filaments constitute one of the shorter cell sides 5, are wound about the corresponding filament from the neighboring cell in the same row, continue as the longer cell side 3 in this lattice cell, are wound about the second filament of this cell, continue as the shorter cell side 5 in the lattice cell in the subsequent row, and so forth until the finish at the other end of the stent. If at even intervals, the filament is wound one half turn more or less about the oppositely extending filament, the filament course is changed from spiral-like into wave-like. The appearance of the lattice cells can be changed according to desire by changing the positions and the number of guide pins 9; the cell shape can, for example, be modified within the framework of the description for FIGS. 1 and 2. Endeavors are made to ensure that, typically, the longer cell sides 3 and the shorter cell sides 5 have a rectilinear course as far as possible between the curves at the guide pins 9, but in practice, the cell sides may have an S-shaped or any other curved course.

In the preferred embodiment, when first converging cell sides 3 and second cell sides 5 are preferably of equal length, first angle α is preferably 90°, and second angle β is preferably 270°. Although, practically, first and second angles α and β can vary somewhat from the preferred angles of 90° and 270°, respectively, the sum of angles α and β should preferably be in a specified range of approximately 345° to 360°. If the sum of the first and second angles α and β are not in the specified range of approximately 345° to 360°, a cell in the tubular-shaped stent can have differing radial stiffness within a cell. For example, should first angle α be 120° and second angle β be 290°, then the sum of the first and second angles α and β would be 410°. At all expanded diameters of the tubular-shaped stent, the first converging cell sides 3 will be more circumferentially, laterally, or transversely oriented than second shorter cell sides 5. As a result, the more circumferentially oriented cell sides 3 have greater radial stiffness than second cell sides 5 in the tubular-shaped stent. Accordingly, the radial stiffness can vary within the cell, and the distribution of the radial stiffness along the axial length of a tubular-shaped stent is not consistent, uniform, or even. This can prevent a self-expanding, tubular-shaped stent from obtaining its optimal expanded shape in vivo due to the fact that the radial force exerted by the stent to the elastic vessel wall is not constant. Similarly, the lateral bending stiffness along the axial length of the stent can vary, much the same way as the radial stiffness.

Furthermore, should the sum of first and second angles $\alpha$ and $\beta$ not be in the specified range of 345° to 360°, each cell within a self-expanding, tubular-shaped stent exhibits mechanical instability during radial compression and/or expansion.

Figure 10:
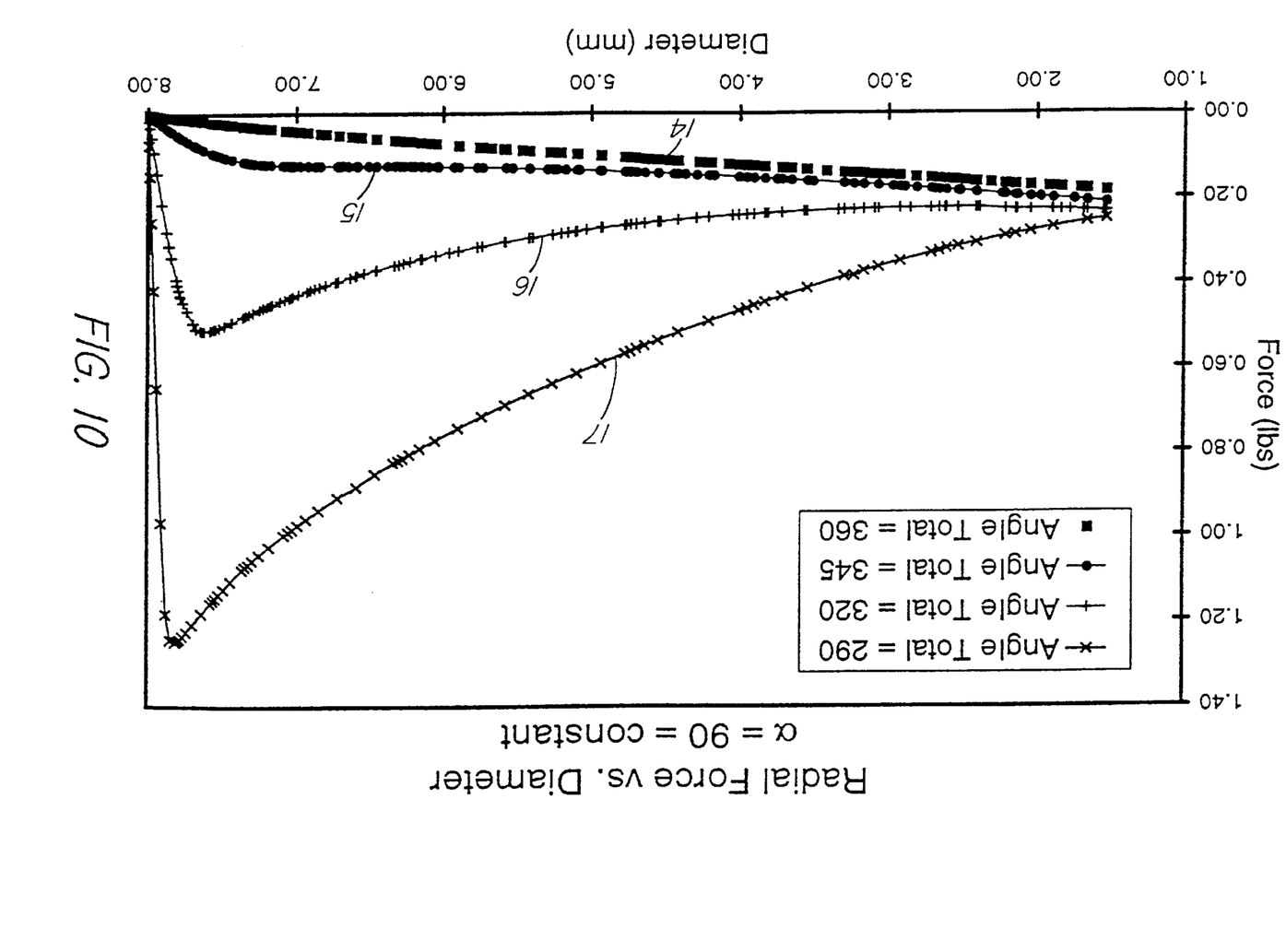
FIG. 10 illustrates various radial force versus stent diameter curves of a stent of the present invention in which the sum of internal cell angles α and β is varied from a preferred sum of 360°.

FIG. 10 depicts radial force versus stent diameter curves 14–17. Radial force versus stent diameter curve 14 is illustrative of when the sum of first and second angles $\alpha$ and $\beta$ equals 360° ($\Sigma(\alpha+\beta)=360°$). In these illustrative examples, a self-expanding tubular-shaped stent was selected with a stent diameter (d) of approximately 8 mm, a first angle $\alpha$ of constant 90°, four cells (N) around the circumference of the stent, and a heart point-to-heart point distance (2A) of 0.247 mm. As depicted between an expanded stent diameter of 8.0 mm and a compressed stent diameter of 1.5 mm, radial force versus stent diameter curve 14 of a preferred self-expanding stent exhibits a smooth, predictable expansion or compression of the stent. Force versus diameter curve 14 exhibits preferred behavior for a stable, self-expanding stent during expansion and compression.

A stable, self-expanding stent has a cell structure that can readily be compressed and inserted into an introducer sheath or expanded therefrom without cells or cell sides uncontrollably jutting or extending into or out of the wall of the tubular-shaped stent. This uncontrollable or unpredictable behavior is characteristic of an unstable stent cell structure and can prevent proper placement of the stent in a vessel. An unstable cell structure with one or more cells or cell sides extending into the passage of a stent can prevent continued delivery or expansion of the remaining cells from the introducer sheath. Similarly, the unstable cell structure can distort the wall of the stent so that the stent cannot be drawn back into the introducer sheath. This situation in a critical vessel can cause trauma or even death to a patient within minutes. The lack of continued delivery or stent withdrawal in less critical vessels can then require open and invasive surgical procedures, again indicative of trauma and complications for the patient.

Should the force versus diameter curve of a given stent exhibit peaks or be discontinuous, then the contraction and expansion of the self-expanding stent is not as predictable as the preferred stable stent. The larger or higher the peaks in the force versus diameter curve, the more unpredictable the behavior of the stent becomes.

Force versus diameter curve 15 of FIG. 10 illustrates a limiting example of when the sum of the angles $\alpha$ and $\beta$ is 345°. The curve illustrates when unstable behavior can occur with resulting inward or outward jutting of selected cells into or out of the stent wall.

Force versus diameter curves 16 and 17 of FIG. 10 illustrate unstable cell structures for self-expanding stents where the sums of the first and the second angles $\alpha$ and $\beta$ are 320° and 290°, respectively. As the sum of the angles deviates more and more from the preferred sum of 360°, the peaks become higher or larger, and the expansion and compression behavior of an unstable stent cell structure becomes more uncontrolled and unpredictable. The behavior of an unstable stent is mirrored when the sum of the angles is in excess of 360°.

Figure 12:
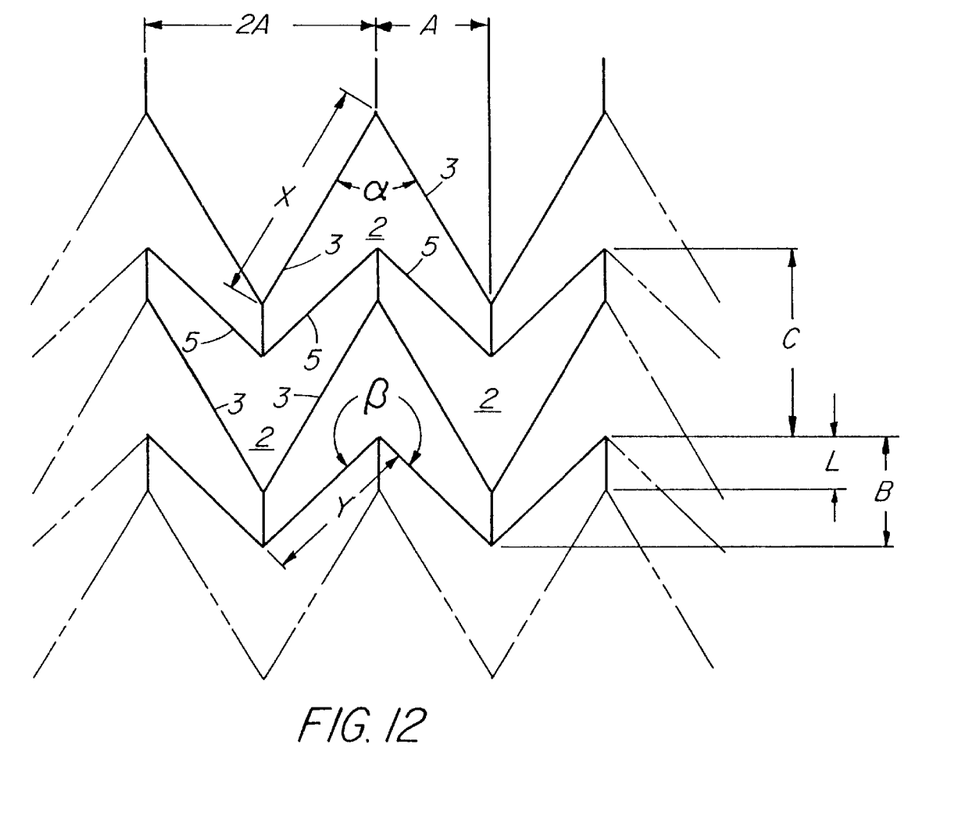
FIG. 12 depicts relative dimensions for the various components of the stent body of the present invention.

FIG. 12 depicts the relative dimensioning and placement of the various components of the tubular-shaped stent body 1. For the illustrated cell structures, the following indicated relationships are provided.

d=Diameter of stent
N=Number of cells around circumference of stent
2A=πd/N
tan(180-β/2)=A/B
Y=[A²+B²]^{1/2}
tan(α/2)=A/(B+C-2L)
X=[(C+B-2L)²+A²]^{1/2}

For the illustrated cell structure, the following values apply.

| Alpha | Beta | Alpha + Beta | Diam. (mm) | No. Cells | 2A (mm) | A (mm) | B (mm) | C (mm) | L (mm) | X (mm) | Y (mm) |
|---|---|---|---|---|---|---|---|---|---|---|---|
| Alpha = 90 degrees = constant | | | | | | | | | | | |
| 90 | 190 | 280 | 8 | 4 | 6.28 | 3.14 | 0.27 | 5.76 | 1.45 | 4.44 | 3.15 |
| 90 | 210 | 300 | 8 | 4 | 6.28 | 3.14 | 0.84 | 5.20 | 1.45 | 4.44 | 3.25 |
| 90 | 255 | 345 | 8 | 4 | 6.28 | 3.14 | 2.41 | 3.63 | 1.45 | 4.44 | 3.96 |
| 90 | 270 | 360 | 8 | 4 | 6.28 | 3.14 | 3.14 | 2.90 | 1.45 | 4.44 | 4.44 |
| Beta = 270 degrees = constant | | | | | | | | | | | |
| 15 | 270 | 285 | 8 | 4 | 6.28 | 3.14 | 3.14 | 23.62 | 1.45 | 24.07 | 4.44 |
| 35 | 270 | 305 | 8 | 4 | 6.28 | 3.14 | 3.14 | 9.72 | 1.45 | 10.45 | 4.44 |
| 75 | 270 | 345 | 8 | 4 | 6.28 | 3.14 | 3.14 | 3.85 | 1.45 | 5.16 | 4.44 |
| 90 | 270 | 360 | 8 | 4 | 6.28 | 3.14 | 3.14 | 2.90 | 1.45 | 4.44 | 4.44 |

The axial length of a self-expanding, tubular-shaped stent remains constant during compression or expansion thereof only when the sum of first and second angles $\alpha$ and $\beta$ equals 360°. Furthermore, a self-expanding stent in which the sum of the angles equals 360°, has a uniform expansion rate along the entire axial length of the stent. Otherwise, a self-expanding stent will exhibit changes in axial length when compressed or expanded. The magnitude of the first and second angles $\alpha$ and $\beta$, the diameter (d) of the stent, and the relative difference between angles $\alpha$ and $\beta$ determine how much the axial length of the stent changes.

Should it be desired to increase the radial stiffness of a preferred, self-expanding stent having a stable cell structure ($\Sigma(\alpha+\beta)=360°$), an increase in first angle $\alpha$ will increase the radial stiffness of the stent. However, second angle $\beta$ must correspondingly decrease to maintain a stable cell structure where the sum of the first and the second angles $\alpha$ and $\beta$ remains in the specified range of 345° to 360°.

Figure 11:
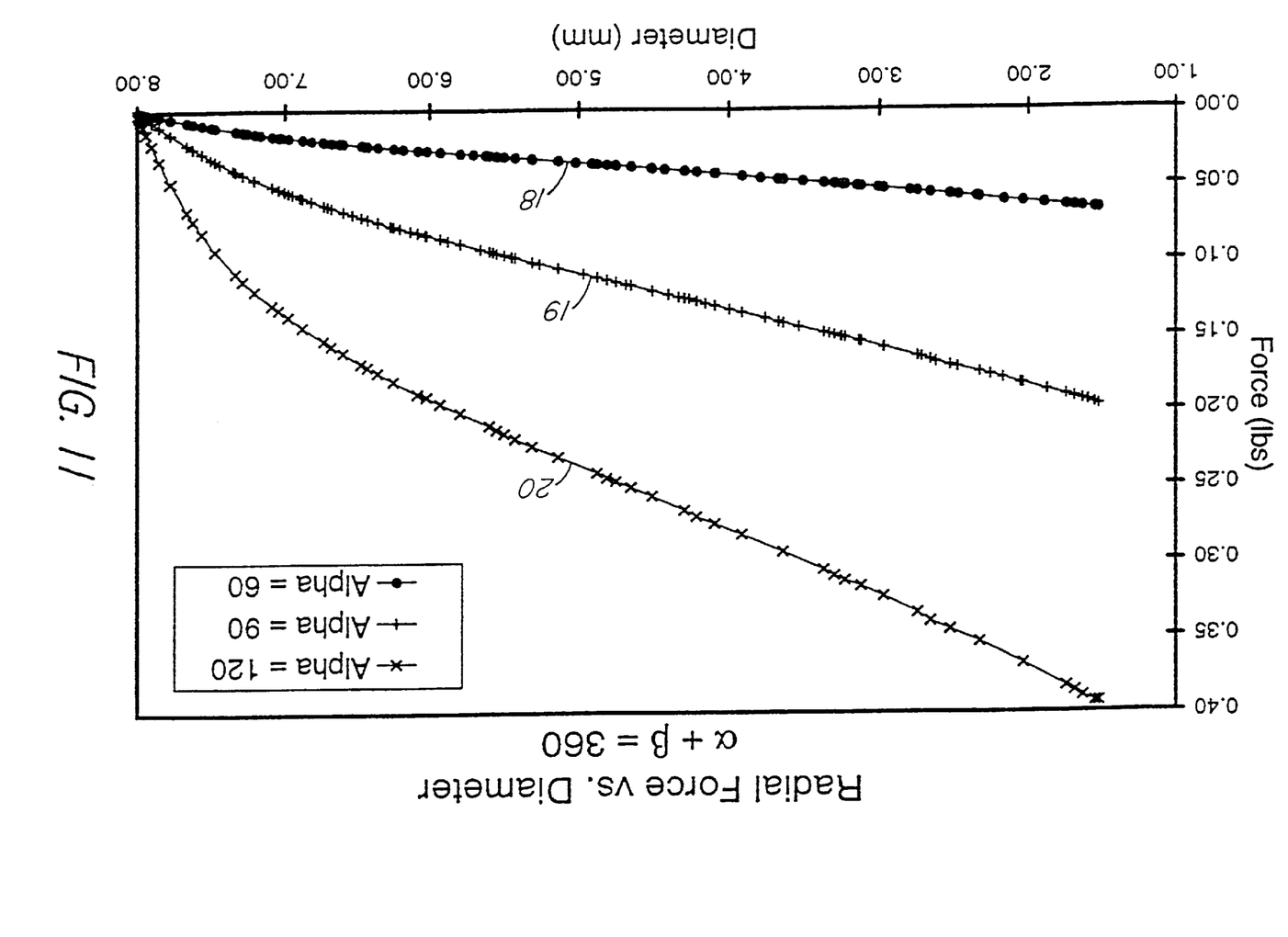
FIG. 11 illustrates various radial force versus stent diameter curves illustrating how radial stiffness of a stent can be varied by varying first angle α and maintaining the sum of angles α and β at 360°.

FIG. 11 illustrates radial force versus stent diameter curves 18–20 when the sum of the first and second angles $\alpha$ and $\beta$ are 360°. Curve 18 illustrates when first angle $\alpha$ is 60°. To increase radial stiffness as suggested, first angle $\alpha$ is increased to 90° (preferred). Curve 19, illustrative of when first angle $\alpha$ is 90°, illustrates that additional force is required to compress a tubular-shaped stent over that of curve 18. To further increase the radial stiffness of a stent, the first angle $\alpha$ is selected as 120°, as illustrated by curve 20. Again, it can be noted that even more radial force is required to compress a tubular-shaped stent than that of a stent depicted in curves 18 and 19.

Figure 4:
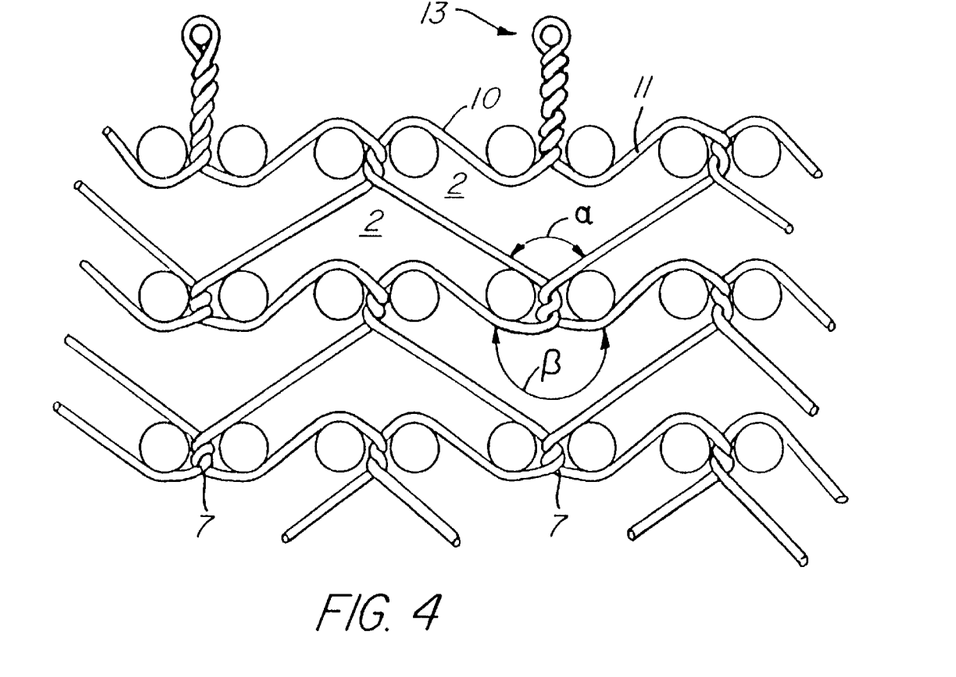
FIG. 4 is a section corresponding to that of FIG. 3 of a stent having a more dense lattice structure.

FIG. 4 shows an example of a varied cell shape in which the first angle $\alpha$ is about 120°, and the second angle $\beta$ is about 253°. It is also seen that the side sections 7 are shorter owing to a smaller pitch in the windings. If long side sections are desired, the filaments may be wound several turns about each other. Instead of winding the filaments about each other, the interconnections between the lattice cells can be rings or threads locking the two adjacent filaments together. A further cell shape is shown in FIG. 5, where the first angle $\alpha$ is about 70°, and the second angle is about 322°. Such a design can be advantageous if the filament diameter is relatively large and the filament thus less flexible.

Figure 6:
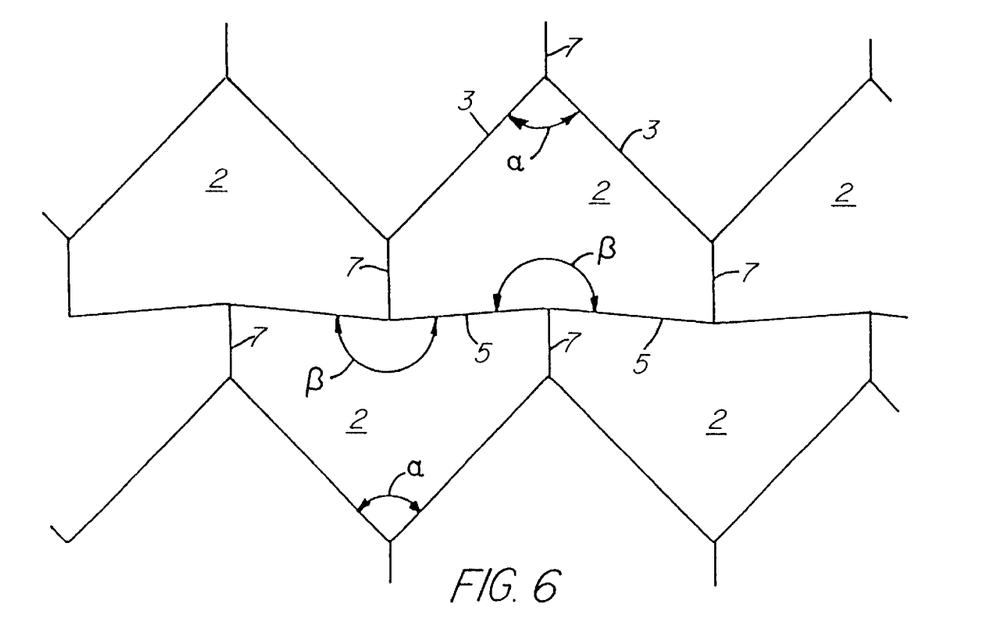
FIGS. 6 and 7 are outlines of two unfolded lattice sections illustrating the effect of varying the angle between the two shorter lattice sides.
Figure 7:
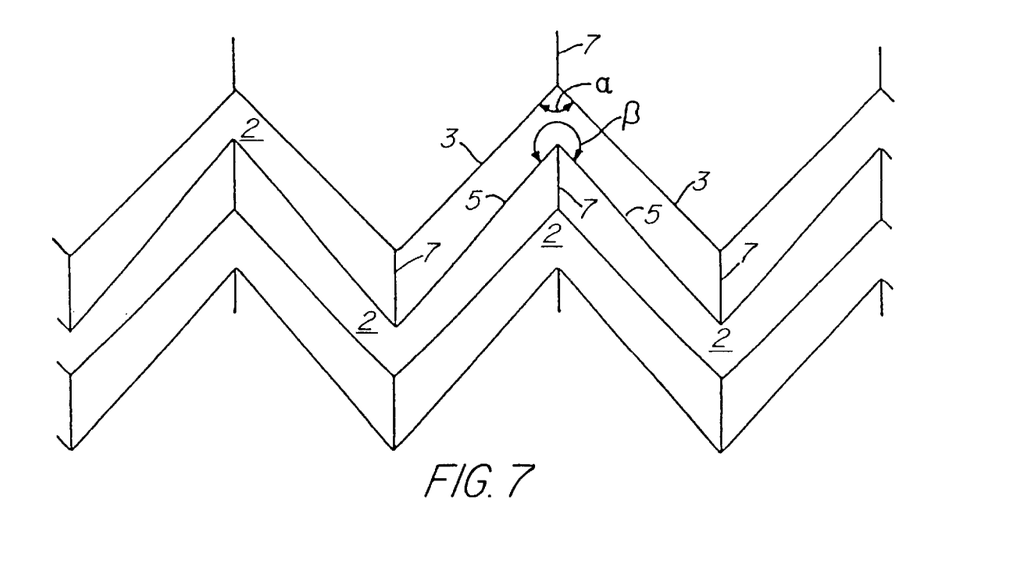

In a comparison between the two embodiments shown in FIGS. 6 and 7, the influence of the second angle $\beta$ on the cell shape is seen when the cell width, the first angle $\alpha$ and the length of the side sections 7 are kept unchanged in relation to the embodiment of FIG. 3. In FIG. 6, the second angle $\beta$ is about 184°, and in FIG. 7 about 275°. In FIG. 6, the lattice structure is open, and the shorter cell sides form slightly curved, annular bands giving the body 1a high pressure rigidity. In FIG. 7, the lattice structure is very dense and enables the body to over-expand heavily.

Figure 8:
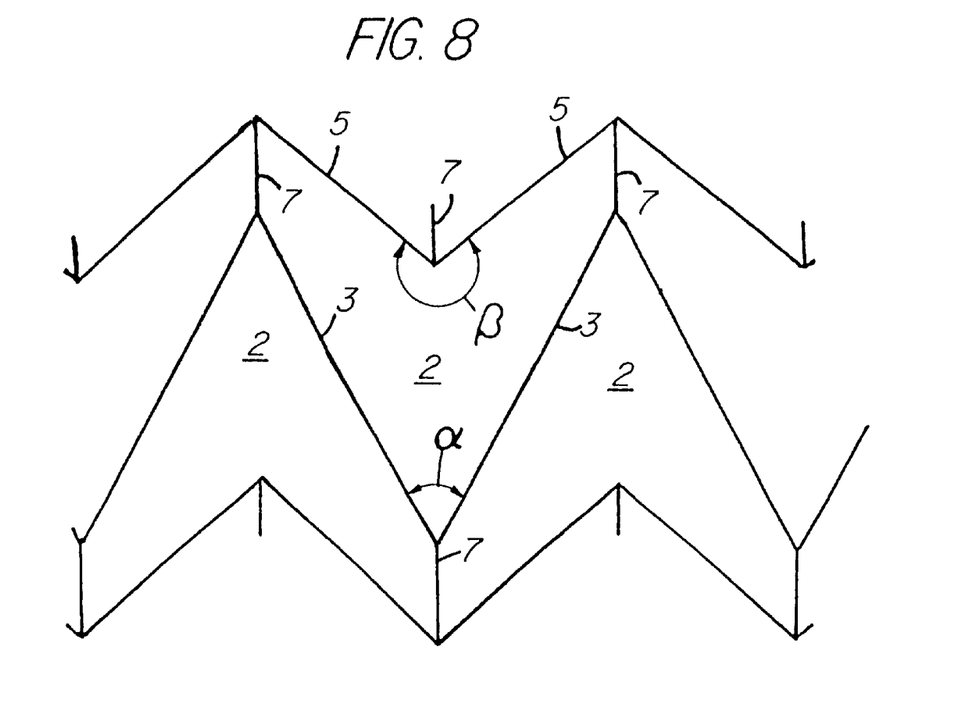
FIGS. 8 and 9 are corresponding outlines for illustration of the effect of varying the angle between the two longer lattice sides.
Figure 9:
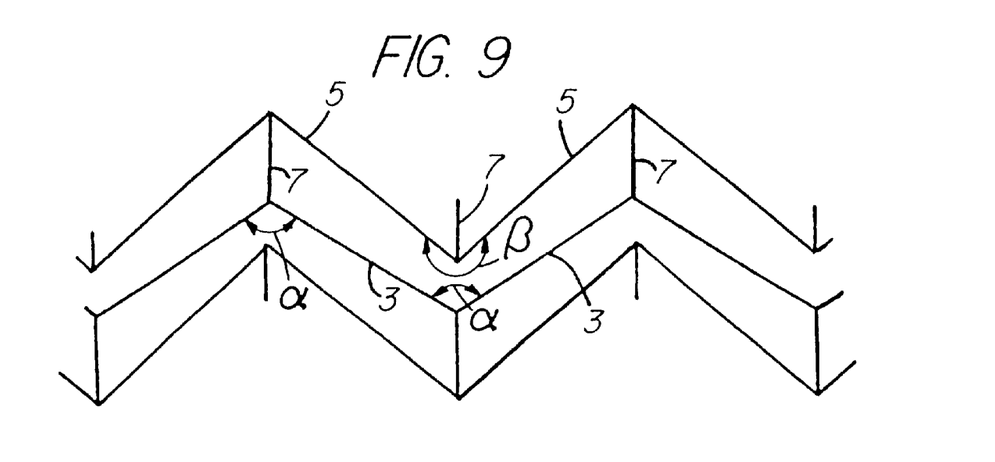

In a comparison between the two embodiments shown in FIGS. 8 and 9, the influence of the first angle $\alpha$ on the cell shape is seen when the cell width, the second angle and the length of the side sections 7 are kept unchanged in relation to the embodiment of FIG. 3. In FIG. 8, the first angle $\alpha$ is about 62°, while in FIG. 9 it is about 120°. In FIG. 8, the cells have a very open structure. In FIG. 9, the structure is very dense, but the amount of wire is also large in comparison to the length of the stent.

The stent material is preferably nitinol, which has excellent elastic properties including superelasticity and can tolerate large deformations. Alternatively, stainless steel, titanium, copper alloys, tantalum or other biologically compatible materials capable of maintaining the expanded state inside the vessel, or mixtures of such materials can be used. If the stent is balloon-expanded at the positioning in the vessel, stainless steel can be just as suitable as nitinol. It is also possible to use a synthetic material as the stent material, such as modified butadiene or another synthetic material with good resilient properties.

The cross-sectional area of the cell sides is chosen on the basis of the desired diameter, desired rigidity and the cell shape in the stent, a larger cross-sectional area being used at larger diameters, at a larger desired rigidity and/or at more open cells or lower cell number. When the lattice shape shown in FIG. 3 is used for a stent for use in the Iliac, the stent can, for example, have a diameter of 8 mm, there can be four cells in each annular row, and the filament can, for example, be a nitinol wire with a diameter of 0.16 mm. A corresponding stent can be used in bile ducts, the lumen of which is reduced by tumors or fibrosis. Stents can also be used for expanding the oesophagus in patients suffering from malignant dysphagia, for expanding the urinary tracts or other body vessels. A very important field of application is stents for expanding constrictions in blood vessels or for maintaining expanded vasoconstrictions, such as in hard stenosis. The below list mentions examples of applicable stent diameters, etc., for different applications.

| Field of application | Stent diameter |
|---|---|
| Arteries | |
| Coronary | 2–4 mm |
| Iliac | 6–12 mm |
| Femoral | 6–12 mm |
| Renal | 6–12 mm |
| Carotid | 6–12 mm |
| Aortic aneurysm | 15–30 mm |
| Veins | |
| Vena cava | 12–30 mm |
| Vena subclavia | 12–30 mm |
| Arteriovenous shunt endoprosthesis | 6–14 mm |
| TIPS (by-pass in liver) | 10–12 mm |
| Urology | |
| Ureteral | 4–7 mm |
| Urethral | 4–7 mm |
| Gastroenterology | |
| Oesophageal | 18 mm at the middle |
| Biliary | 6–10 mm |
| Pancreatic | 2–3 mm |
| Thorax | |
| Bronchial | 15–20 mm |

The filament diameter or the thickness/width of the cell sides is adapted to the stent diameter, the cell sides being given less cross-sectional area at smaller stent diameters. The filament diameter may, for example, be in the interval of 0.06–0.40 mm.

It is possible to supplement the stent with a sheath of a suitably tight material, such as Dacron, PTFE or another suitable biocompatible material. The use of such a graft on a stent is well-known in the art and needs no further description.

What is claimed is:

1. An expandable stent comprising a flexible, tubular-shaped body (1) with a longitudinal axis and at least two ends, a wall of the body being formed by interconnected, closed lattice cells (2) arranged with at least two cells laterally adjacent to each other, each closed lattice cell (2) having first elongated, mutually converging cell sides (3) which form a first angle ($\alpha$) therebetween, the body including filament-shaped lattice material in which the stent is expandable from a radially compressed state having a first diameter into a radially expanded state having a second diameter larger than said first diameter, wherein the lattice material in at least two of the lattice cells (2) forms a generally arrowhead-like shape with second interconnected cell sides (5) which form a second angle ($\beta$) therebetween and are positioned opposite to and interconnected with the first mutually converging cell sides (3).

2. An expandable stent according to claim 1, wherein arrowheads (4) are oriented in a longitudinal direction of the body (1), and wherein an interval between two neighboring lattice cells with the same orientation of the arrowheads (4) consists of a lattice cell with an opposite orientation of the arrowhead (4).

3. An expandable stent according to claim 2, wherein the lattice cells (2) adjacent to each other in an annular row in the circumferential direction of the body (1) have alternatingly oriented arrowheads (4) and constitute a lattice pattern repeated along the length of the body.

4. An expandable stent according to claim 1, wherein each of the second cell sides (5) have substantially a second length (Y), and that each of the first converging cell sides (3) have a first length (X).

5. An expandable stent according to claim 4, wherein the first and the second lengths (X,Y) are equal.

6. An expandable stent according to claim 4, wherein the first and the second lengths (X,Y) are different.

7. An expandable stent according to claim 1, wherein said first angle ($\alpha$) between the first converging cell sides (3) and facing into the cell is in a range of 20° to 160°, and wherein said second angle ($\beta$) between the second cell sides (5) and facing into the cell is in a range of 184° to 340°.

8. An expandable stent according to claim 7, wherein the first angle ($\alpha$) is in a range of 60° to 120° and wherein the second angle ($\beta$) is in a range of 210° to 320°.

9. An expandable stent according to claim 7, wherein the sum of the first angle ($\alpha$) and the second angle ($\beta$) is in a range of 345° to 360°.

10. An expandable stent according to claim 9, wherein the sum of the first angle ($\alpha$) and the second angle ($\beta$) is 360°.

11. An expandable stent according to claim 7 wherein the first angle ($\alpha$) is 90° and wherein the second angle ($\beta$) is 270°.

12. An expandable stent according to claim 7, wherein the first converging cell sides (3) and the second cell sides (5) all form an angle of between 10° and 45° with the longitudinal direction of the body (1).

13. An expandable stent according to claim 12, wherein the first cell sides (3) form an angle of between 40° and 45° with the longitudinal direction.

14. An expandable stent according to claim 1, wherein the first angle ($\alpha$) in the lattice cells (2) is smaller in one area of the body (1) than in another area of the body.

15. An expandable stent according to claim 1, wherein the second angle ($\beta$) in the lattice cells (2) is larger in one area of the body (1) than in another area of the body, and wherein the second angle ($\beta$) is larger at end areas of the body.

16. An expandable stent according to claim 1, wherein at at least one end of the body (1) the first and second cell sides (3, 5) of the lattice cells (2) are of greater length and/or the lattice cells (2) have a smaller angle ($\beta$) between the second cell sides (5) than at a middle portion of the body, whereby the body has a larger diameter at the end than at the middle portion.

17. An expandable stent according to claim 1, wherein a number (N) of lattice cells (2) in an annular row in a circumferential direction of the body (1) substantially corresponds to a radius of the body measured in mm.

18. An expandable stent according to claim 1, wherein the body (1) is formed by several filaments (10, 11) constituting the first and the second cell sides (3, 5) and being wound about each other at adjacent ends of pairs of first and second cell sides.

19. An expandable stent according to claim 18, wherein each filament (10, 11) has a stepped spiral-like or a stepped wave-like course in the longitudinal direction of the body (1).

20. An expandable stent according to claim 1, wherein the body (1) is formed from a thin-walled tube or a thin-walled piece of plate in which the cell openings (2) are fashioned.

21. An expandable/collapsible stent with a tubularly-shaped body formed from at least two series of closed lattice cells, at least one series of closed lattice cells each comprising a general arrowhead-shape having interconnected cell sides which form a first angle ($\alpha$) therebetween and mutually converging cell sides which form a second angle ($\beta$) therebetween, the cells further having laterally interconnected cell sides, and with cells of one series adjacent to cells of the at least one other series and having cell sides in common, the orientation of the adjacent sides being such that when the at least two series are radially compressed or expanded there is no significant longitudinal expansion or contraction of the stent.

22. A stent according to claim 21, wherein the lattice cells of one series are oriented in opposite directions to those of adjacent series, and wherein cells of the said one series are off-set relative to adjacent cells in adjacent series.

23. A stent according to claim 22, wherein the cells of each series collectively form a waveform pattern with peaks and troughs, and wherein the peaks of the cells of one series fit into the troughs of the cells of an adjacent series.

24. A stent according to claim 23, wherein at least one of the peaks and troughs of each series are at least one of being angled, rounded, and flattened.

25. A stent according to claim 23, wherein the peaks are angled substantially 90°.

* * * * *